US006172251B1

(12) United States Patent
Parker

(10) Patent No.: US 6,172,251 B1
(45) Date of Patent: Jan. 9, 2001

(54) SOLID/LIQUID PHASE TRANSFER SYSTEM

(75) Inventor: Dane Kenton Parker, Massillon, OH (US)

(73) Assignee: The Goodyear Tire & Rubber Company, Akron, OH (US)

( * ) Notice: Under 35 U.S.C. 154(b), the term of this patent shall be extended for 0 days.

(21) Appl. No.: 09/340,528

(22) Filed: Jun. 28, 1999

Related U.S. Application Data

(60) Provisional application No. 60/094,000, filed on Jul. 24, 1998.

(51) Int. Cl.$^7$ .................................. C07F 7/08; C07F 7/18
(52) U.S. Cl. ................................................. 556/427
(58) Field of Search .............................. 556/427

(56) References Cited

U.S. PATENT DOCUMENTS

| | | | |
|---|---|---|---|
| 3,842,111 | 10/1974 | Meyer-Simon et al. | 260/448.2 |
| 3,873,489 | 3/1975 | Thurn et al. | 260/33.6 |
| 3,978,103 | 8/1976 | Meyer-Simon et al. | 260/448.8 |
| 5,405,985 | 4/1995 | Parker et al. | 556/427 |
| 5,468,893 | 11/1995 | Parker et al. | 556/427 |
| 5,583,245 | * 12/1996 | Parker et al. | 556/427 |
| 5,663,396 | 9/1997 | Musleve et al. | 556/427 |
| 6,114,560 | * 9/2000 | Ichinohe et al. | 556/427 |

* cited by examiner

Primary Examiner—Paul F. Shaver

(74) Attorney, Agent, or Firm—Alvin T Rockhill

(57) ABSTRACT

The present invention discloses a technique for reacting a first liquid chemical compound with a second liquid chemical compound which comprises (1) supporting the first liquid chemical compound on a solid support; (2) subsequently bringing the solid support into contact with the second liquid chemical compound; and (3) allowing the first chemical compound to react with the second chemical compound in the presence of a phase transfer catalyst to produce a reaction product. This technique is particularly useful in the synthesis of sulfur containing organosilicon compounds of the formula Z-Alk-$S_n$-Alk-Z wherein Z is selected from the group consisting of

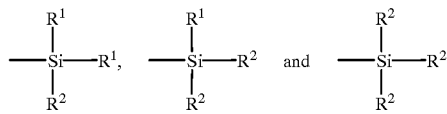

wherein $R^1$ is an alkyl group of 1 to 4 carbon atoms, cyclohexyl or phenyl; wherein $R^2$ is alkoxy group of 1 to 8 carbon atoms, cycloalkoxy group of 5 to 8 carbon atoms or an alkylmercapto group of 1 to 8 carbon atoms; wherein Alk is a divalent hydrocarbon of 1 to 18 carbon atoms; and wherein n is an integer of 2 to 8. For instance, such sulfur containing organosilicon compounds can be made by reacting aqueous solutions of various polysulfidic anions in saturated sodium chloride brine solutions with chloropropyltriethoxysilane (CPTES) supported on carbon black in the presence of a phase transfer catalyst.

23 Claims, No Drawings

SOLID/LIQUID PHASE TRANSFER SYSTEM

This application claims the benefit of Provisional Application No. 60/094,000 filed Jul. 24, 1998.

BACKGROUND OF THE INVENTION

Rubber compositions often contain a filler, such as carbon black or silica, to attain desired physical properties. For instance, the rubber compositions used in tires normally contain one or more fillers. Carbon black has traditionally been used as a filler in manufacturing tires. However, there is a growing trend toward utilizing silica or a combination of silica and carbon black in tire rubbers to attain improved physical properties, such as wet traction characteristics.

A silica coupling agent is normally employed in rubber compounds that utilize silica as a filler in order to attain more optimal physical characteristics. Various sulfur containing organosilicon compounds are useful as reactive coupling agents. The use of such organosilicon compounds in silica containing rubbers improves physical properties by coupling the silica filler to the rubber. It should be noted that certain organosilicon compounds are also useful as adhesion primers for glass, metals and other substrates.

U.S. Pat. Nos. 3,842,111, 3,873,489 and 3,978,103 disclose the preparation of various sulfur containing organosilicon compounds. These organosilicon compounds are prepared by reacting (1) 2 moles of a compound of the formula:

Z-Alk-X wherein X is a halogen selected from the group consisting of chlorine, bromine or iodine; wherein Z is

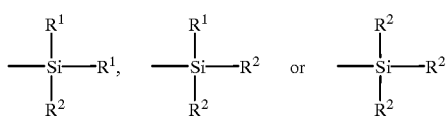

wherein $R^1$ is an alkyl group containing from 1 to 4 carbon atoms or a phenyl group and wherein $R^2$ is an alkoxy group containing from 1 to 8 carbon atoms, a cycloalkoxy group containing from 5 to 8 carbon atoms or an alkylmercapto group containing from 1 to 8 carbon atoms, wherein Alk is a divalent aliphatic hydrocarbon, an unsaturated hydrocarbon or a cyclic hydrocarbon containing 1 to 18 carbon atoms; with (2) 1 mole of a compound of the formula

$M_2S_n$ wherein M is an ammonium group or a metal atom and n is a whole number from 2 to 6. Since the two starting materials are liquid, the reaction can take place in the absence of a solvent; however, the utilization of a volatile inert organic solvent is preferred and accordingly such an inert organic solvent is generally used. The reaction is carried out with the exclusion of water. The reason for the exclusion of water is to avoid the alkaline hydrolysis reaction of the silyl alkoxy groups which will ultimately lead to insoluble polymeric by-products and lower the overall yield of desired product. Aliphatic alcohols, such as methanol, ethanol, iso-propyl alcohol, normal-propyl alcohol, n-butanol, iso-butanol and t-butyl alcohol are representative examples of suitable inert organic solvents. At the end of the reaction between the two starting materials, the separated salt is removed by filtration. The filtrate is then freed from the solvent by distillation under vacuum. Unfortunately, this process is difficult to carry out on a commercial basis for a variety of reasons. For instance, most alcohols that are suitable for utilization as the solvent are difficult to obtain and maintain in a water-free (anhydrous) state. Additionally, most suitable alcohols, such as ethyl alcohol, have a low flash point which is highly undesirable in commercial applications.

U.S. Pat. No. 5,405,985 relates to a process for the production of organosilicon compounds of the formula

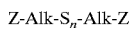

Z-Alk-$S_n$-Alk-Z in which Z is selected from the group consisting of

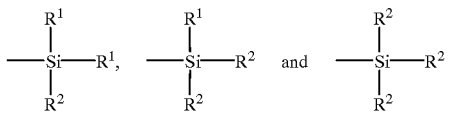

where
  $R_1$ is an alkyl group of 1 to 4 carbon atoms, cyclohexyl or phenyl;
  $R_2$ is alkoxy of 1 to 8 carbon atoms or cycloalkoxy of 5 to 8 carbon atoms;
  Alk is a divalent hydrocarbon of 1 to 18 carbon atoms and n is an integer of 2 to 8; comprising reacting (A) a compound of the formula

Z-Alk-X where X is Cl, Br or I; with (B) a compound of the formula

$Me_2S_n$ where Me is an ammonium ion or an alkali metal ion; and wherein the reaction is conducted in the presence of a phase transfer catalyst and an aqueous phase.

U.S. Pat. No. 5,468,893 relates to a process for the production of organosilicon compounds of the formula

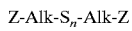

Z-Alk-$S_n$-Alk-Z in which Z is selected from the group consisting of

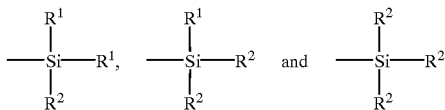

where
  $R_1$ is an alkyl group of 1 to 4 carbon atoms, cyclohexyl or phenyl;
  $R_2$ is alkoxy of 1 to 8 carbon atoms or cycloalkoxy of 5 to 8 carbon atoms;
  Alk is a divalent hydrocarbon of 1 to 18 carbon atoms and n is an integer of 2 to 8; comprising reacting (A) a compound of the formula

Z-Alk-X when X is Cl, Br or I; with (B) a compound of the formula

$Me_2S_n$ where Me is ammonium or an alkali metal;
  wherein the reaction is conducted in the presence of a phase transfer catalyst, an aqueous phase and a salt of the formula

XY or

X$_2$SO$_4$ where X is selected from the group consisting of Li, Na, K, Rb and Cs; and where Y is selected from the group consisting of F, Cl and Br.

U.S. Pat. No. 5,663,396 discloses a process for the production of organosilicon compounds of the formula Z-Alk-S$_n$-Alk-Z  (I)

in which Z is selected from the group consisting of

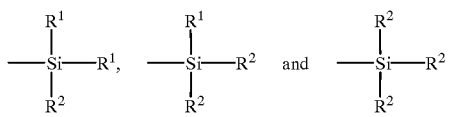

where

R$^1$ is an alkyl group of 1 to 4 carbon atoms, cyclohexyl or phenyl;

R$^2$ is alkoxy of 1 to 8 carbon atoms, or cycloalkoxy of 5 to 8 carbon atoms;

Alk is a divalent hydrocarbon of 1 to 18 carbon atoms and n is an integer of 2 to 8; comprising (A) reacting sodium hydroxide with sulfur in the presence of a saturated NaCl aqueous solution to form a reaction mixture; and (B) reacting said reaction mixture with a compound of the formula:

Z-Alk-X  (II)

where X is Cl or Br in the presence of a phase transfer catalyst.

SUMMARY OF THE INVENTION

The present invention is based upon the discovery that sulfur containing organosilicon compounds that are suitable for use as silica coupling agents can be readily prepared in excellent yield by phase transfer catalysis in the presence of a filler, such as carbon black. The natural advantages of the phase transfer process with regard to speed, purity and simplicity can be retained even in the presence of substantial levels of the filler. It has been further discovered that the presence of the filler allows for the elimination of both the brine solution and the organic solvent. If the ratio of the final product to the filler is properly adjusted, a supported product that is heavily loaded can be obtained. The filler takes the functional place of the solvent in the process of this invention.

Even though solvent is not required, the use of aqueous brine is still preferred for optimum yield. The final supported product is isolated as a dry free-flowing solid suitable for direct use in conventional rubber mixing equipment. This is advantageous since most customers of silica coupling agents prefer or require that the silane coupling agent be in solid form for simplified handling and use in conventional rubber mixing equipment. This new method greatly simplifies the two-step techniques described by the prior art and reduces processing complexity. Cost reduction is also achieved since the unit operation of blending on a carrier, such as carbon black, is eliminated.

This invention more specifically discloses a process for the production of sulfur containing organosilicon compounds of the formula Z-Alk-S$_n$-Alk-Z wherein Z is selected from the group consisting of

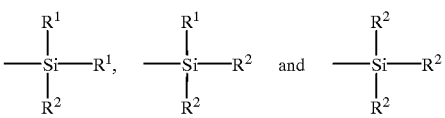

wherein R$^1$ is an alkyl group containing from 1 to 4 carbon atoms, a cyclohexyl group or a phenyl group; wherein R$^2$ is alkoxy group containing from 1 to 8 carbon atoms, a cycloalkoxy group containing from 5 to 8 carbon atoms or an alkylmercapto group containing from 1 to 8 carbon atoms; wherein Alk is a divalent hydrocarbon of containing from 1 to 18 carbon atoms; and wherein n is an integer from 2 to 8; said process comprising reacting a compound of the formula Me$_2$S$_n$ with a compound of the formula Z-Alk-X; wherein Me represents an alkali metal or an ammonium ion, wherein X represents a halogen selected from the group consisting of fluorine, chlorine, bromine and iodine; wherein said reaction is carried out in the presence of a phase transfer catalyst; wherein said process is carried out in the presence of an aqueous phase containing a salt of the formula MX or M$_2$SO$_4$; wherein M represents a metal selected from the group consisting of lithium, sodium, potassium, rubidium and cesium; wherein X represents a halogen selected from the group consisting of fluorine, chlorine, bromine and iodine; and wherein said reaction is carried out in the presence of a filler.

The present invention further discloses a process for the production of organosilicon compounds of the formula Z-Alk-S$_n$-Alk-Z wherein Z is selected from the group consisting of

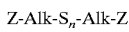 

wherein R$^1$ is an alkyl group containing from 1 to 4 carbon atoms, a cyclohexyl group or a phenyl group; wherein R$^2$ is alkoxy group containing from 1 to 8 carbon atoms, cycloalkoxy group containing from 5 to 8 carbon atoms or an alkylmercapto group containing from 1 to 8 carbon atoms; wherein Alk is a divalent hydrocarbon containing from 1 to 18 carbon atoms; and wherein n is an integer from 2 to 8; said process comprising reacting a compound of the formula Z-Alk-X with the reaction product made by reacting sodium hydroxide with sulfur in a saturated sodium chloride solution; wherein Me represents an alkali metal or an ammonium ion; wherein X represents a halogen selected from the group consisting of fluorine, chlorine, bromine and iodine; wherein said reaction is carried out in the presence of a phase transfer catalyst; and wherein said reaction is carried out in the presence of a filler.

In another embodiment of this invention, the organosilicon compound is synthesized in the absence of organic solvents and the filler. The filler is subsequently added to the reaction mixture produced in the synthesis of the organosilicon compound. Supported organosilicon compound can then be recovered from the reaction mixture by separating the filler from the reaction mixture. This separation of the supported organosilicon compound can be easily carried out since the supported organosilicon compound is in the form of a solid material and the other components of the reaction mixture are in liquid form. Accordingly, the supported organosilicon compound can be conveniently removed by filtration, decantation or the like.

This invention also discloses a process for the production of supported organosilicon compounds of the formula

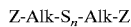
Z-Alk-S$_n$-Alk-Z wherein Z is selected from the group consisting of

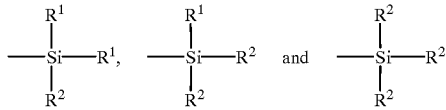

wherein R$^1$ is an alkyl group containing from 1 to 4 carbon atoms, a cyclohexyl group or a phenyl group; wherein R$^2$ is alkoxy group containing from 1 to 8 carbon atoms, cycloalkoxy group containing from 5 to 8 carbon atoms or an alkylmercapto group containing from 1 to 8 carbon atoms; wherein Alk is a divalent hydrocarbon containing from 1 to 18 carbon atoms; and wherein n is an integer from 2 to 8; said process comprising the steps of (1) reacting a compound of the formula Me$_2$S$_n$ with a compound of the formula Z-Alk-X to produce a reaction mixture containing said organosilicon compound; wherein Me represents an alkali metal or an ammonium ion; wherein X represents a halogen selected from the group consisting of fluorine, chlorine, bromine and iodine; wherein said reaction is carried out in the presence of a phase transfer catalyst; wherein said process is carried out in the presence of an aqueous phase containing a salt of the formula MY or M$_2$SO$_4$; wherein M represents a metal selected from the group consisting of lithium, sodium, potassium, rubidium and cesium; wherein X represents a halogen selected from the group consisting of fluorine, chlorine, bromine and iodine; and wherein said process is carried out in the absence of organic solvents; (2) adding a filler to the reaction mixture; and (3) recovering the supported organosilicon compound from the reaction mixture.

This invention also further reveals a process for the production of supported sulfur containing organosilicon compounds of the formula Z-Alk-S$_n$-Alk-Z, wherein Z is selected from the group consisting of

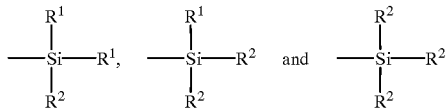

wherein R$^1$ is an alkyl group containing from 1 to 4 carbon atoms, a cyclohexyl group or a phenyl group; wherein R$^2$ is alkoxy group containing from 1 to 8 carbon atoms, a cycloalkoxy group containing from 5 to 8 carbon atoms or an alkylmercapto group containing from 1 to 8 carbon atoms; wherein Alk is a divalent hydrocarbon containing from 1 to 18 carbon atoms; and wherein n is an integer from 2 to 8; said process comprising the steps of (1) reacting a compound of the formula Z-Alk-X with the reaction product made by reacting sodium hydroxide with sulfur in a saturated sodium chloride solution to produce a reaction mixture containing said organosilicon compound; wherein said reaction is carried out in the presence of a phase transfer catalyst; and wherein said process is carried out in the absence of organic solvents; (2) adding a filler to the reaction mixture; and (3) recovering the supported organosilicon compound from the reaction mixture.

DETAILED DESCRIPTION OF THE INVENTION

The sulfur containing organosilicon compounds that are synthesized by utilizing the process of this invention are of the formula

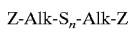
Z-Alk-S$_n$-Alk-Z in which Z is selected from the group consisting of

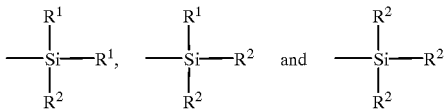

where R$^1$ is an alkyl group containing from 1 to 4 carbon atoms, a cyclohexyl group or a phenyl group; where R$^2$ is an alkoxy group of 1 to 8 carbon atoms, a cycloalkoxy group of 5 to 8 carbon atoms or an alkylmercapto group containing from 1 to 8 carbon atoms; and where Alk is a divalent hydrocarbon of 1 to 18 carbon atoms and where n represents an integer from 2 to 8.

Some representative examples of sulfur containing organosilicon compounds which may be prepared in accordance with the present invention include: 3,3'-bis(trimethoxysilylpropyl) disulfide, 3,3'-bis(triethoxysilylpropyl) tetrasulfide, 3,3'-bis(triethoxysilylpropyl) octasulfide, 3,3'-bis(trimethoxysilylpropyl) tetrasulfide, 2,2'-bis(triethoxysilylethyl) tetrasulfide, 3,3'-bis(trimethoxysilylpropyl) trisulfide, 3,3'-bis(triethoxysilylpropyl) trisulfide, 3,3'-bis(tributoxysilylpropyl) disulfide, 3,3'-bis(trimethoxysilylpropyl) hexasulfide, 3,3'-bis(trimethoxysilylpropyl) octasulfide, 3,3'-bis(trioctoxysilylpropyl) tetrasulfide, 3,3'-bis(trihexoxysilylpropyl) disulfide, 3,3'-bis(tri-2"-ethylhexoxysilylpropyl) trisulfide, 3,3'-bis(triisooctoxysilylpropyl) tetrasulfide, 3,3'-bis(tri-t-butoxysilylpropyl) disulfide, 2,2'-bis(methoxy diethoxy silyl ethyl) tetrasulfide, 2,2'-bis(tripropoxysilylethyl) pentasulfide, 3,3'-bis(tricyclonexoxysilylpropyl) tetrasulfide, 3,3'-bis(tricyclopentoxysilylpropyl) trisulfide, 2,2'-bis(tri-2"-methylcyclohexoxysilylethyl) tetrasulfide, bis(trimethoxysilylmethyl) tetrasulfide, 3-methoxy ethoxy propoxysilyl 3'-diethoxybutoxy-silylpropyltetrasulfide, 2,2'-bis(dimethyl methoxysilylethyl) disulfide, 2,2'-bis(dimethyl sec.butoxysilylethyl) trisulfide, 3,3'-bis(methyl butylethoxysilylpropyl) tetrasulfide, 3,3'-bis(di t-butylmethoxysilylpropyl) tetrasulfide, 2,2'-bis(phenyl methyl methoxysilylethyl) trisulfide, 3,3'-bis(diphenyl isopropoxysilylpropyl) tetrasulfide, 3,3'-bis(diphenyl cyclohexoxysilylpropyl) disulfide, 3,3'-bis(dimethyl ethylmercaptosilylpropyl) tetrasulfide, 2,2'-bis(methyl dimethoxysilylethyl) trisulfide, 2,2'-bis(methyl ethoxypropoxysilylethyl) tetrasulfide, 3,3'-bis(diethyl methoxysilylpropyl) tetrasulfide, 3,3'-bis(ethyl di-sec.butoxysilylpropyl) disulfide, 3,3'-bis(propyl diethoxysilylpropyl) disulfide, 3,3'-bis(butyl dimethoxysilylpropyl) trisulfide, 3,3'-bis(phenyl dimethoxysilylpropyl) tetrasulfide, 3-phenyl ethoxybutoxysilyl 3'-trimethoxysilylpropyl tetrasulfide, 4,4'-bis (trimethoxysilylbutyl) tetrasulfide, 6,6'-bis (triethoxysilylhexyl) tetrasulfide, 12,12'-bis (triisopropoxysilyl dodecyl) disulfide, 18,18'-bis (trimethoxysilyloctadecyl) tetrasulfide, 18,18'-bis (tripropoxysilyloctadecenyl) tetrasulfide, 4,4'-bis (trimethoxysilyl-buten-2-yl) tetrasulfide, 4,4'-bis (trimethoxysilylcyclohexylene) tetrasulfide, 5,5'-bis (dimethoxymethylsilylpentyl) trisulfide, 3,3'-bis (trimethoxysilyl-2-methylpropyl) tetrasulfide and 3,3'-bis (dimethoxyphenylsilyl-2-methylpropyl) disulfide.

The preferred sulfur containing organosilicon compounds which are prepared in accordance with the present invention are the 3,3'-bis(trimethoxy or triethoxy silylpropyl) polysulfides. The most preferred sulfur containing organosilicon compound is 3,3'-bis(triethoxysilylpropyl) disulfide. Therefore, with respect to the formula Z-Alk-$S_n$-Alk-Z, it is preferred for Z to represent

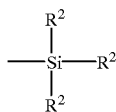

where $R^2$ is an alkoxy of 2 to 4 carbon atoms, with 2 carbon atoms being particularly preferred; Alk is a divalent hydrocarbon of 2 to 4 carbon atoms with 3 carbon atoms being particularly preferred; and n is an integer of from 2 to 6 with 2 being particularly preferred.

Sodium hydroxide can be reacted with sulfur in the presence of a saturated aqueous sodium chloride (NaCl) solution to produce an aqueous reaction product. It is believed that the sulfur may react with the sodium hydroxide to form an intermediate polysulfidic ion which subsequently reacts with the haloalkylsilane. By varying the molar ratio of the sulfur to sodium hydroxide, one can control the resultant reaction product. Generally speaking, the molar ratio of the sulfur to sodium hydroxide ranges from 4:1 to 1:28. If one desires a higher concentration of a disulfide product (where n is 2), one uses a molar excess of sodium hydroxide, such as a molar ratio of 1:16. If one desires a higher concentration of a tetrasulfide product (where n is 4), one uses a higher concentration of sulfur; for example, 1:1 to 4:1. In any case, this procedure can be employed to produce compounds of the formula $Me_2S_n$ wherein n represents an integer from 1 to 8, with n preferably being an integer from 2 to 6.

As mentioned above, the reaction between the sodium hydroxide and sulfur is conducted in the presence of a saturated aqueous sodium chloride solution (brine). The volume of brine that is present may vary. The concentration of the two reactants in the brine generally ranges from about 20 to 50 percent by weight. Preferably, the concentration of the sodium hydroxide and sulfur in the brine ranges from about 25 to 45 percent.

The reaction between the sodium hydroxide and sulfur may be conducted at a variety of temperatures. Generally speaking, the reaction is conducted at a temperature ranging from about 75 to 100° C. Preferably, the reaction is conducted at a temperature ranging from about 85 to 95° C. The reaction between the sodium hydroxide and sulfur is a relatively quick reaction. For example, the complete reaction may range from about 5 to 30 minutes.

Once the reaction between the sodium hydroxide and sulfur is complete and the polysulfidic ions are formed, the reaction mixture can be further reacted with a halogenated silane of formula Z-Alk-X, wherein Z is selected from the group consisting of

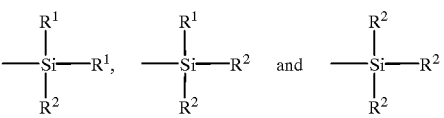

wherein $R^1$ is an alkyl group containing from 1 to 4 carbon atoms, a cyclohexyl group or a phenyl group; wherein $R^2$ is alkoxy group containing from 1 to 8 carbon atoms, a cycloalkoxy group containing from 5 to 8 carbon atoms or an alkylmercapto group of 1 to 8 carbon atoms; wherein Alk is a divalent hydrocarbon containing from 1 to 18 carbon atoms; and wherein X represents a halogen selected from the group consisting of chlorine, fluorine, bromine and iodine.

Some representative examples of halogenated silanes of formula Z-Alk-X include the halogenated (chloro and bromo) substituted forms of ethyl triethoxy silane, propyl triethoxy silane, butyl triethoxy silane, pentyl triethoxy silane, hexyl triethoxy silane, heptyl triethoxy silane, octyl triethoxy silane, nonyl triethoxy silane, decyl triethoxy silane, undecyl triethoxy silane, dodecyl triethoxy silane, tridecyl triethoxy silane, tetradecyl triethoxy silane, pentadecyl triethoxy silane and the like.

By varying the molar ratio of the halogenated silane to the reaction mixture containing the polysulfidic ion, one can control the resultant reaction product. Generally speaking, the molar ratio of the halogenated silane to polysulfidic ion ranges from 1:1 to greater than 1:5. If one desires a higher concentration of a disulfide product (where n is 2), one uses a molar ratio of 1:3 or greater. If one desires a higher concentration of a tetrasulfide product (where n is 4), one uses a lower molar excess of polysulfidic ion.

The reaction between the halogenated silane of the formula Z-Alk-X and the polysulfidic ion is conducted in the presence of a phase transfer catalyst. Representative phase transfer catalysts may have a quaternary onium cation of the following structural formulae (I), (II) or (III):

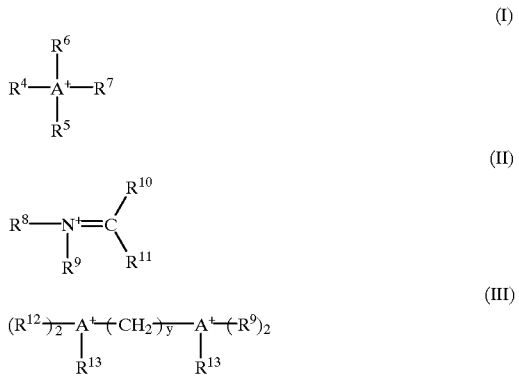

wherein A represents nitrogen, phosphorus or arsenic; $R^4$, $R^5$, $R^6$ and $R^7$, which may be the same or different, are each a linear or branched chain alkyl radical containing from 1 to 16 carbon atoms, optionally substituted with a phenyl, hydroxyl, halo, nitro, alkoxy or alkoxycarbonyl substituent; a linear or branched chain alkenyl radical containing from 2 to 12 carbon atoms, preferably from 4 to 8 carbon atoms and most preferably an alkenyl radical derived from the starting material conjugated diene; an aryl radical containing from 6 to 10 carbon atoms, optionally substituted by one or more alkyl substituents containing from 1 to 4 carbon atoms or alkoxy, alkoxycarbonyl or halo substituents; and with the proviso that any two of said radicals $R^4$ to $R^7$ may together form a single linear or branched chain alkylene, alkenylene or alkadienylene radical containing from 3 to 6 carbon atoms; $R^8$, $R^9$, $R^{10}$ and $R^{11}$, which also may be the same or different, are each a linear or branched chain alkyl radical containing from 1 to 4 carbon atoms; with the proviso that the $R^{10}$ and $R^{11}$ radicals may together form an alkylene radical containing from 3 to 6 carbon atoms; and with the further proviso that the $R^9$ and $R^{10}$ or $R^9$ and $R^{11}$ radicals may together form an alkylene, alkenylene or alkadienylene radical containing 4 carbon atoms and, together with the nitrogen atom, comprising a 5-membered nitrogen heterocycle; $R^{12}$ is a linear or branched chain alkyl radical containing from 1 to 4 carbon atoms, or a phenyl radical; $R^{13}$ is a linear or branched chain alkyl radical containing from 1 to 4 carbon atoms which may be the same or different from $R^{12}$ or $R^{13}$ may be a linear or branched chain alkenyl radical containing from 2 to 12 carbon atoms, preferably from 4 to 8 carbon atoms, and more preferably an alkenyl radical derived by carbonylation of a conjugated diene; and y is an integer of from 1 to 10, and preferably less than or equal to 6.

Some representative examples of the quaternary onium cations of structural Formula I include the following: tetramethylammonium, triethylmethylammonium, tributylmethylammonium, trimethyl(n-propyl)ammonium, tetraethylammonium, tetrabutylammonium, dodecyltrimethylammonium, methyltrioctylammonium, heptyltributylammonium, tetrapropylammonium, tetrapentylammonium, tetrahexylammonium, tetraheptylammonium, tetraoctylammonium, tetradecylammonium, butyltripropylammonium, methyltributylammonium, pentyltributylammonium, methyldiethylpropylammonium, ethyldimethylpropylammonium, tetradodecylammonium, tetraoctadecylammonium, hexadecyltrimethylammonium, benzyltrimethylammonium, benzyldimethylpropylammonium, benzyldimethyloctylammonium, benzyltributylammonium, benzyltriethylammonium, phenyltrimethylammonium, benzyldimethyltetradecylammonium, benzyldimethylhexadecylammonium, dimethyldiphenylammonium, methyltrialkyl($C_8$–$C_{10}$) ammonium, methyltriphenylammonium, buten-2-yltriethylammonium, N,N-dimethyltetramethyleneammonium, N,N-diethyltetramethyleneammonium, tetramethylphosphonium, tetrabutylphosphonium, ethyltrimethylphosphonium, trimethylpentylphosphonium, trimethylpentylphosphonium, octyltrimethylphosphonium, dodecyltrimethylphosphonium, trimethylphenylphosphonium, diethyldimethylphosphonium, dicyclohexyldimethylphosphonium, dimethyldiphenylphosphonium, cyclohexyltrimethylphosphonium, triethylmethylphosphonium, methyl-tri(isopropyl)phosphonium, methyl-tri(n-propyl)phosphonium, methyl-tri(n-butyl)phosphonium, methyl-tri(2-methylpropyl)phosphonium, methyltricyclohexylphosphonium, methyltriphenylphosphonium, methyltribenzyl phosphonium, methyl-tri(4-methylphenyl)phosphonium, methyltrixylylphosphonium, diethylmethylphenylphosphonium, dibenzylmethylphenylphosphonium, ethyltriphenylphosphonium, tetraethylphosphonium, ethyl-tri(n-propyl)phosphonium, triethylpentylphosphonium, hexadecyltributylphosphonium, ethyltriphenylphosphonium, n-butyl-tri(n-propyl) phosphonium, butyltriphenylphosphonium, benzyltriphenylphosphonium, (β-phenylethyl) dimethylphenylphosphonium, tetraphenylphosphonium, triphenyl(4-methylphenyl)phosphonium, tetrakis (hydroxymethyl)phosphonium, tetrakis(2-hydroxyethyl) phosphonium and tetraphenylarsonium.

Exemplary of the Formula II cations are the following: N-methylpyridinium, N-ethylpyridinium, N-hexadecylpyridinium and N-methylpicolinium.

Some representative examples of cations of structural Formula III include the following: 1,2-bis (trimethylammonium)ethane, 1,3-bis(trimethylammonium) propane, 1,4-bis(trimethylammonium)butane and 1,3-bis (trimethylammonium)butane.

Representative of the anions of said onium salts include the following ions: $F^-$, $ClO_4^-$, $PF_6^-$, $BF_4^-$, tetraphenylborate anion, $PO_4^{-3}$, $HPO_4^{-2}$, $H_2PO_4^-$, $CH_3SO_3^-$,

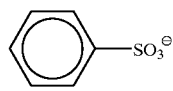

$HSO_4^-$, $NO_3^-$, $SO_4^{-2}$, $Cl^-$ and $Br^-$. Preferably, the anion is $Cl^-$ or $Br^-$. A particularly preferred onium salt that is used is tetrabutyl ammonium bromide.

The amount of onium salt that is used in the process of the present invention may vary. Generally speaking, the amount of onium salt will range from about 0.1 to 10 mol percent relative to the halogenated silane of formula Z-Alk-X with an amount within the range of 1 to 5 mole percent being preferred.

The phase transfer catalyst may be added to the reaction at any time. From a practical standpoint, the catalyst is preferably added to the reaction mixture all at once or portionwise at a temperature which is within the range of 65° C. to 90° C. as a solid or concentrated (40–50 percent) aqueous solution.

In practicing this invention, the reaction between the polysulfidic ion and the halogenated silane of formula Z-Alk-X can be carried out as a solid/liquid phase transfer reaction. A filler, such as carbon black or silica, is employed as the solid component for the solid/liquid phase transfer reaction. Thus, such reactions are carried out in the presence of the liquid aqueous phase and a filler as the solid phase. After the reaction has been completed, the sulfur containing organosilicon compound produced can be easily separated from the aqueous phase since it is supported on the filler. This separation can be done by filtration or decantation. It is accordingly not necessary for the phase transfer reaction to be conducted in the presence of any organic solvents. The phase transfer reaction of this invention will accordingly be carried out in the absence of organic solvents, such as toluene, xylene, benzene, heptane, octane, decane and chlorobenzene.

As mentioned above, the reaction between the halogenated silane of formula Z-Alk-X and the reaction mixture containing the polysulfidic ion is conducted in the presence of an aqueous phase. The volume of water that is present may vary and may be the volume of saturated aqueous sodium chloride solution from the first reaction. The concentration of the two reactants (Z-Alk-X and polysulfidic ion) in the aqueous phase generally ranges from about 20 to 50 percent by weight. Preferably, the concentration of the sulfide and sulfur in the aqueous phase ranges from about 25 to 45 percent.

For the reaction between the polysulfidic ion and the Z-Alk-X compound, additional amounts (in addition to the sodium chloride present in the brine for the first reaction) may be added. Examples of such salts include those of the formula MX and the formula $M_2SO_4$ wherein M is selected from the group consisting of lithium, sodium, potassium, rubidium and cesium; and wherein X is selected from the group consisting of fluorine, chlorine, bromine and iodine. It is normally preferred for X to represent chlorine or bromine with it being most preferred for X to represent chlorine. Representative examples of such salts include LiF, LiCl, LiBr, $Li_2SO_4$, NaF, NaCl, NaBr, $Na_2SO_4$, KF, KCl, KBr, $K_2SO_4$, RbCl, RbBr, $Rb_2SO_4$, CsCl, CsBr and $Cs_2SO_4$. Whereas the amount of salt may vary, the salt is generally present in an amount ranging from 10 percent by weight of the aqueous solution to full or complete saturation of the aqueous solution. Obviously, an excess of salt (more than full saturation) may be used; however, no additional benefit has been found. In addition, as one can appreciate, all of the various salts mentioned above have varying levels of solubility in an aqueous solution; however, the solubility of such salts are well known. In the context of saturation of the aqueous phase, it should be calculated at the desired reaction temperature since solubility of such salts in an aqueous phase are related to the temperature of the aqueous phase. Preferably, the amount of salt that is present in the aqueous phase ranges from 20 weight percent to complete or full saturation. If supplemental salt is desired, it may be added to the reaction vessel at any time so long as it is present during the reaction.

In accordance with the preferred embodiment of the present invention, the polysulfidic ion and salt are dissolved or dispersed in the aqueous phase. A filler, such as carbon black or silica is then added, followed by the halogenated silane compound of formula Z-Alk-X. The mixture is then heated, optionally under an inert atmosphere. The mixture may be heated to a temperature ranging from about 60° C. to 100° C., with a temperature of from 75° C. to 95° C. being preferred. The appropriate amount of phase transfer catalyst is then added to the reaction mixture as a solid or as a concentrated aqueous solution. The progress of the reaction may then be followed by gas chromatography or other analytical techniques. Upon filtration, the filtrate is separated into the aqueous phase and solid phase containing the desired product.

In another embodiment of this invention, the filler is added after the chemical reaction between the polysulfidic ion and the halogenated silane has been completed. This is accomplished by dispersing the filler throughout the aqueous reaction medium after the sulfur containing organosilicon compound has been synthesized. The sulfur containing organosilicon compound then becomes bound onto the filler and is supported thereby. The supported organosilicon compound can then, of course, be recovered from the aqueous reaction medium by filtration or decantation.

In addition to the polysulfidic ion and halogenated silane, an additional reactant of the formula:

Alk-X where X is a halogen as previously defined may be present in those instances where unsymmetrical organosilicon compound s are desired in addition to those organosilicon compounds of formula Z-Alk-$S_n$-Alk-Z.

The unsymmetrical organosilicon compounds are of the formula

Alk-$S_n$-Alk-Z where n, Alk and Z are as previously defined. As can be appreciated, Alk is a divalent hydrocarbon of 1 to 18 carbon atoms; and, therefore, to avoid duplication, the representative list of unsymmetrical compounds incorporate "alkyl" in their name whereas one skilled in the art appreciates it would be methyl, ethyl, propyl, butyl, etc, and up to octyldecyl, depending on the reactants used. Such representative unsymmetrical compounds include: 3-(trimethoxysilyl)-n-propyl-n-alkyl disulfide, 3-(triethoxysilyl)propyl-n-alkyl tetrasulfides, 3-(triethoxysilyl)propyl-n-alkyl octasulfides, 3-(trimethoxysilyl)propyl-n-alkyl tetrasulfides, 2-(triethoxysilyl)ethyl-n-alkyl tetrasulfides, 3-(trimethoxysilyl)propyl-n-alkyl trisulfides, 3-(triethoxysilyl)propyl-n-alkyl trisulfides, 3-(tributoxysilyl)propyl-n-alkyl disulfides, 3-(trimethoxysilyl)propyl-n-alkyl hexasulfides, 3-(trimethoxysilyl)propyl-n-alkyl octasulfides, 3-(trioctoxysilyl)propyl-n-alkyl tetrasulfides, 3-(trihexoxysilyl)propyl-n-alkyl disulfides, 3-(triisooctoxysilyl)propyl-n-alkyl tetrasulfides, 3-(tri-t-butoxysilyl)propyl-n-alkyl disulfides, 2-(methoxy diethoxy silyl)ethyl-n-alkyl tetrasulfides, 2-(tripropoxysilyl)ethyl-n-alkyl pentasulfides, 3-(tricyclonexoxysilyl)propyl-n-alkyl tetrasulfides, 3-(tricyclopentoxysilyl)propyl-n-alkyl trisulfides, 2-(dimethyl methoxysilyl)ethyl-n-alkyl disulfides, 2-(dimethyl sec.butoxysilyl)ethyl-n-alkyl trisulfides, 3-(methyl butylethoxysilyl)propyl-n-alkyl tetrasulfides, 3-(di t-butylmethoxysilyl)propyl-n-alkyl tetrasulfides, 2-(phenyl methyl methoxysilyl)ethyl-n-alkyl trisulfides, 3-(diphenyl isopropoxysilyl)propyl)-n-alkyl tetrasulfides, 3-(diphenyl cyclohexoxysilyl)propyl-n-alkyl disulfides, 3-(dimethyl ethylmercaptosilyl)propyl-n-alkyl tetrasulfides, 2-(methyl dimethoxysilyl)ethyl-n-alkyl trisulfides, 2-(methyl ethoxypropoxysilyl)ethyl-n-alkyl tetrasulfides, 3-(diethyl methoxysilyl)propyl-n-alkyl tetrasulfides, 3-(ethyl di-sec. butoxysilyl)propyl-n-alkyl disulfides, 3-(propyl diethoxysilyl)propyl-n-alkyl disulfides, 3-(butyl dimethoxysilyl)propyl-n-alkyl trisulfides, 3-(phenyl dimethoxysilyl)propyl-n-alkyl tetrasulfides, 4-(trimethoxysilyl)butyl-n-alkyl tetrasulfide, 6-(triethoxysilyl)hexyl-n-alkyl tetrasulfides, 12-(trisopropoxysilyl)dodecyl-n-alkyl disulfides, 18-(trimethoxysilyloctadecyl) n-alkyl tetrasulfides, 18-(tripropoxysilyl)octadecenyl-n-alkyl tetrasulfides, 4-(trimethoxysilyl-buten-2-yl)-n-alkyl tetrasulfides, 4-(trimethoxysilyl)cyclohexylene-n-alkyl tetrasulfides, 5-(dimethoxymethylsilyl)pentyl-n-alkyl trisulfides, 3-(trimethoxysilyl-2-methylpropyl)-n-alkyl tetrasulfides and 3-(dimethoxyphenylsilyl)-2-methylpropyl-n-alkyl disulfides.

This invention is illustrated by the following working examples which are presented merely for the purpose of illustration and are not intended to limit the scope of the invention. Unless specifically indicated otherwise, parts and percentages are given by weight.

EXAMPLE 1

In this experiment, bis(3-triethoxysilylpropyl) tetrasulfide was synthesized and recovered on solid carbon black utilizing the technique of this invention. In the procedure used, a 3-liter, three-neck, round-bottomed flask equipped with a mechanical paddle stirrer, reflux condenser, thermometer and dropping funnel was charged with 65 grams (0.5 moles) of $Na_2S*2.7\ H_2O$, 48 grams (1.5 moles) of sulfur and 1000 ml of water. This mixture was then stirred with heating to 85–95° C. until a uniform dark red sodium tetrasulfide solution had formed. The solution was then cooled to 75° C.

and 269 grams of Pig 399 carbon black was added. After reheating to 82° C., a mixture of 228.4 grams (0.95 moles) of chloropropyltriethoxy silane (CPTES) and 11.3 grams (0.0243 moles) of Adogen 464 tetrabutylammonium bromide (phase transfer catalyst) was added to the reaction mixture by means of a dropping funnel over a 20-minute period. The mixture was reacted another 30 minutes after the addition was completed. The mixture was then filtered to remove the carbon black phase. The aqueous phase was pale yellow and contained no separate liquid phase of the bis(3-triethoxysilylpropyl) tetrasulfide synthesized. The bis(3-triethoxysilylpropyl) tetrasulfide can be represented by the formula: $((CH_3CH_2O)_3SiCH_2CH_2CH_2S_2)_2$. The carbon black phase was then washed with three 400 ml portions of water before being dried at 40° C. in a circulating air oven overnight. This procedure resulted in the isolation of 508 grams of loaded product which represents a yield of 47 percent.

For purposes of NMR analysis, 20 grams of the loaded carbon black was continuously extracted with toluene in a soxhlet apparatus overnight. The yellow extract was then stripped on a rotovac to remove most of the toluene before a final high vacuum-stripping. This resulted in the recovery of 8.93 grams of amber-colored oil. The amount of sulfur in the product as determined by $C_{13}$ NMR analysis is shown in Table I.

TABLE I

| S Atoms in Product | Mole Fraction | # of S Atoms |
| --- | --- | --- |
| $S_2$ | 0.179 | 0.359 |
| $S_3$ | 0.280 | 0.840 |
| $S_4$ | 0.267 | 1.068 |
| $S_5$ | 0.165 | 0.822 |
| $S_6$ | 0.073 | 0.440 |
| $S_7$ & $S_8$ | 0.036 | 0.269 |
| Total | 1.000 | 3.798 |

EXAMPLE 2

The procedure described in Example 1 was repeated in this experiment except at ½ scale and except for the fact that the carbon black was added at the very beginning along with the sodium sulfide, sulfur and water. After stirring for 30 minutes at about 85–90° C,. the mixture was filtered. The loaded carbon black cake was washed with water and dried in a circulating air oven. After drying, a 20-gram sample of this material was toluene extracted and worked-up for analysis as previously described. The amount of sulfur in the product as determined by $C_{13}$ NMR analysis is shown in Table II.

TABLE II

| S Atoms in Product | Mole Fraction | # of S Atoms |
| --- | --- | --- |
| $S_2$ | 0.173 | 0.345 |
| $S_3$ | 0.268 | 0.803 |
| $S_4$ | 0.262 | 1.050 |
| $S_5$ | 0.156 | 0.777 |
| $S_6$ | 0.103 | 0.619 |
| $S_7$ & $S_8$ | 0.038 | 0.288 |
| Total | 1.000 | 3.883 |

EXAMPLE 3

In this experiment, bis(3-triethoxysilylpropyl) disulfide was synthesized and recovered on solid carbon black utilizing the technique of this invention. In the procedure used, a 3-liter, three-neck, round-bottomed flask equipped with a mechanical paddle stirrer, reflux condenser, thermometer and dropping funnel was charged with 28.16 grams (0.37 moles) of commercially hydrated sodium hydrosulfide, 2.95 grams (0.092 moles) of sulfur, 54.0 grams of Pig 399 carbon black, 60.0 grams (0.25 moles) of chloropropyltriethoxy silane (CPTES) and 148 ml of water. This mixture was then stirred with heating to 85–95° C. for 20 minutes before 5.0 grams (0.0078 moles) of 50 percent aqueous tetrabutyl ammonium bromide solution was added over a one-minute period. After the catalyst addition, the mixture was reacted for another 25 minutes at 85° C. before the mixture was filtered and washed with water. The product was then dried at 40° C. in a circulating air oven overnight with 105 grams of carbon black loaded product being isolated.

For purposes of NMR analysis, 20 grams of the bis(3-triethoxysilylpropyl) disulfide loaded carbon black was continuously extracted with toluene to isolate 8.0 grams of material. NMR analysis of this material indicated a relatively high level of residual CPTES as well as a higher than expected trisulfide and tetrasulfide content. The amount of sulfur in the product as determined by $C_{13}$ NMR analysis is shown in Table III.

TABLE III

| S Atoms in Product | Mole Fraction | # of S Atoms |
| --- | --- | --- |
| $S_2$ | 0.696 | 1.393 |
| $S_3$ | 0.223 | 0.670 |
| $S_4$ | 0.066 | 0.262 |
| $S_5$ | 0.015 | 0.074 |
| $S_6$ | 0.000 | 0.000 |
| $S_7$ & $S_8$ | 0.000 | 0.000 |
| Total | 1.000 | 2.399 |

EXAMPLE 4

In this experiment, the technique of this invention was carried out in a 30-gallon (113.5 liter) reactor which was equipped with an overhead condenser. At the beginning of the procedure, a flow of cooling water to the overhead condenser was started and nitrogen was used to purge the reactor. Then, 55 pounds (20.5 kilograms) of water, 20 pounds (7.5 kilograms) of sodium chloride, 6 pounds (2.2 kilograms) of sodium sulfide and 4.5 pounds (1.7 kilograms) of sulfur were charged into the reactor through a sight-glass nozzle. Agitation was started once the water had been charged. After the charging had been completed, the sight-glass was closed and agitation was increased.

The reactor was then heated to an internal temperature which was within the range of 90° C. to 95° C. While the reactor was heating, a mixture of 20 pounds (7.5 kilograms) of chloropropyltriethoxy silane (CPTES) and 684 grams of Adogen 464 tetrabutyl ammonium bromide was prepared in a charge tank. The charge tank was subsequently sealed and pressurized with nitrogen to 20 psig ($2.39 \times 10^5$ Pascals) and the charge tank dip leg was connected to the reactor with braided hose.

After the internal reactor temperature had stabilized within the range of 90° C. to 95° C., it was maintained at that temperature for about 10 minutes and then the mixture from the charge tank was fed into the reactor at a rate of approximately 1.5 pounds per minute (568 grams per minute). It took about 15 minutes to charge the mixture from the charge tank into the reactor. After the reactor had been fully charged, agitation was continued and the temperature was maintained for an additional 10 minutes. Then, the reactor was cooled to a temperature within the range of 60° C. to 70° C., and 22 pounds (8.2 kilograms) of carbon black was added to the reactor. The contents of the reactor were agitated for about 10 minutes and then 14 pounds (5.2 kilograms) of additional water was charged into the reactor from a charge tank. Agitation was continued for an additional 5 minutes and the contents of the reactor were transferred to a centrifuge at a temperature of 60° C. The reactor was flushed with water to capture as much product as possible.

The contents of the reactor were centrifuged and washed with water at 70° C. The weight of water used in washing the product was equal to about three times the product weight. The centrifuge cake of product was reslurried in 15 gallons (56.8 liters) of water at 50° C. and agitated for 10 minutes. The product was centrifuged and washed in cold water. The cake of product recovered was dried at 60° C. for 24 hours and packaged. A theoretical yield of about 91 percent was attained. The product had a moisture content of 0.20 percent, a residual CPTES content of 0.02 percent, contained 41.9 percent extractables, 39.0 percent disulfide, 35.0 percent trisulfide and 26.0 percent polysulfides.

Comparative Example 5

Preparation of Bis-(3-triethoxysilylpropyl) polysulfide

A 1-liter, three-neck, round-bottomed flask equipped with a mechanical paddle stirrer, reflux condenser and thermometer was charged with 12.0 g (0.30 moles) of solid sodium hydroxide pellets, 100 ml of saturated aqueous sodium chloride solution and 6.4 g (0.20 moles) of elemental sulfur. The mixture was stirred while heating to 95° C. and held at this temperature for 10 minutes. A clear red solution formed during this period. The solution was then cooled to 80° C. and a solution of 75 ml of toluene and 48.0 g (0.20 moles) of 3-chloropropyltriethoxysilane (CPTES) was added. The mixture was reheated to 80° C. with continued stirring (ca. 300–400 rpm) before adding 2.0 g (0.00031 moles) of a 50 percent aqueous solution of tetrabutylammonium bromide all at once. The color of the solution immediately turns dark upon addition of the catalyst and the temperature of the reaction mixture gradually increases to 90 to 92° C. within a few minutes before subsiding. The mixture was reacted for a total of 30 minutes after catalyst addition, keeping the reaction temperature at about 80° C. During this period, the formation of some insoluble polymer was noted. Gas chromatographic analysis of the liquid organic phase indicated that the predominant components of the mixture were 57 percent starting material (CPTES), 25.4 percent bis-(3-triethoxysilylpropyl) disulfide (I) and 14.6 percent bis-(3-triethoxysilylpropyl) trisulfide (II). The isolated insoluble polymer weighed 11.9 grams.

Comparative Example 6

Preparation of Bis-(3-triethoxysilylpropyl) polysulfide

The procedure of Comparative Example 5 repeated except that an additional 25 grams of solid sodium chloride was added to the initial ingredients. G.C. analysis of the organic liquid phase showed 69.3 percent starting CPTES, 21.4 percent bis-(3-triethoxysilylpropyl) disulfide and 6.3 percent bis-(3-triethoxysilylpropyl) trisulfide. The isolated insoluble polymer weighed 16.5 grams.

Comparative Example 7

Preparation of Bis-(3-triethoxysilylproyyl) polysulfide

The procedure of Comparative Example 5 was repeated except that the levels of both sulfur and sodium hydroxide were doubled. The mixture refluxed very vigorously at 82° C. G.C. analysis of the organic liquid phase showed results similar to Comparative Example 6. The isolated insoluble polymer weighed 4.0 grams.

Comparative Example 8

Preparation of Bis-(3-triethoxysilylpropyl) polysulfide

The procedure of Comparative Example 5 was repeated except that the sulfur level was doubled and the aqueous solution of the catalyst was added over a period of 1 minute. G.C. analysis of liquid organic phase showed 30.4 percent starting CPTES, 38.2 percent of bis-(3-triethoxysilylpropyl) disulfide and 29.7 percent of bis-(3-triethoxysilylpropyl) trisulfide. No polymer formation was observed.

Comparative Example 9

Preparation of Bis-(3-triethoxysilylpropyl) polysulfide

The procedure of Comparative Example 5 was repeated except that 25.6 g (0.80 moles) of sulfur and 17.0 g (0.425 moles) of sodium hydroxide were used. After 30 minutes, the G.C. analysis indicated substantial CPTES remaining. At this point, another 2.0 g addition of the 50 percent aqueous catalyst solution was added and the mixture stirred at 80° C. for another 30 minutes. G.C. analysis showed only a trace of CPTES with 26.7 percent of bis-(3-triethoxysilylpropyl) disulfide and 65.5 percent of bis-(3-triethoxysilylpropyl) trisulfide. No polymer formation was observed.

After phase separation and removal of the toluene, pale yellow needles (sulfur) crystallized from the crude product (2.4 g). The residual liquid was then stripped under high vacuum (0.15 mm Hg) to an overhead temperature of 110° C. to remove toluene and tri-n-butylamine (catalyst breakdown product) to give 45.1 g of amber liquid. Proton and C-13 NMR analysis of this material indicated the following mole fraction composition:

| | |
|---|---|
| $S_2$ | 0.141 |
| $S_3$ | 0.278 |
| $S_4$ | 0.264 |
| $S_5$ | 0.162 |
| $S_6$ | 0.105 |
| $S_7$–$S_8$ | 0.051 |
| | 1.000 |

Variations in the present invention are possible in light of the description provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A process for the production of organosilicon compounds of the formula Z-Alk-$S_n$-Alk-Z wherein Z is selected from the group consisting of

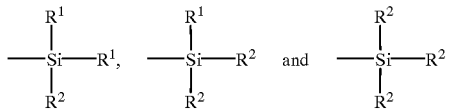

wherein $R^1$ is an alkyl group containing from 1 to 4 carbon atoms, a cyclohexyl group or a phenyl group; wherein $R^2$ is an alkoxy group containing from 1 to 8 carbon atoms, a cycloalkoxy group containing from 5 to 8 carbon atoms or an alkylmercapto group containing from 1 to 8 carbon atoms; wherein Alk is a divalent hydrocarbon containing from 1 to 18 carbon atoms; and wherein n is an integer from 2 to 8; said process comprising reacting a compound of the formula $Me_2S_n$ with a compound of the formula Z-Alk-X; wherein Me represents an alkali metal or an ammonium ion, wherein X represents a halogen selected from the group consisting of fluorine, chlorine, bromine and iodine; wherein said reaction is carried out in the presence of a phase transfer catalyst; wherein said process is carried out in the presence of an aqueous phase containing a salt of the formula MX or $M_2SO_4$; wherein M represents a metal selected from the group consisting of lithium, sodium, potassium, rubidium and cesium; wherein X represents a halogen selected from the group consisting of fluorine, chlorine, bromine and iodine; and wherein said reaction is carried out in the presence of a filler.

2. A process as specified in claim 1 wherein said reaction is carried out in the absence of organic solvents.

3. A process as specified in claim 2 wherein said filler is carbon black.

4. A process for the production of supported organosilicon compounds of the formula Z-Alk-$S_n$-Alk-Z, wherein Z is selected from the group consisting of

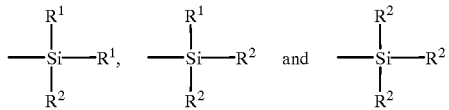

wherein $R^1$ is an alkyl group containing from 1 to 4 carbon atoms, a cyclohexyl group or a phenyl group; wherein $R^2$ is an alkoxy group containing from 1 to 8 carbon atoms, a cycloalkoxy group containing from 5 to 8 carbon atoms or an alkylmercapto group containing from 1 to 8 carbon atoms; wherein Alk is a divalent hydrocarbon containing from 1 to 18 carbon atoms; and wherein n is an integer from 2 to 8; said process comprising the steps of (1) reacting a compound of the formula $Me_2S_n$ with a compound of the formula Z-Alk-X to produce a reaction mixture containing said organosilicon compound; wherein Me represents an alkali metal or an ammonium ion; wherein X represents a halogen selected from the group consisting of fluorine, chlorine, bromine and iodine; wherein said reaction is carried out in the presence of a phase transfer catalyst; wherein said process is carried out in the presence of an aqueous phase containing a salt of the formula MX or $M_2SO_4$; wherein M represents a metal selected from the group consisting of lithium, sodium, potassium, rubidium and cesium; wherein X represents a halogen selected from the group consisting of fluorine, chlorine, bromine and iodine; and wherein said process is carried out in the absence of organic solvents; (2) adding a filler to the reaction mixture; and (3) recovering the supported organosilicon compound from the reaction mixture.

5. A process for the production of organosilicon compounds of the formula Z-Alk-$S_n$-Alk-Z wherein Z is selected from the group consisting of

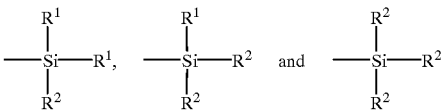

wherein $R^1$ is an alkyl group containing from 1 to 4 carbon atoms, a cyclohexyl group or a phenyl group; wherein $R^2$ is an alkoxy group containing from 1 to 8 carbon atoms, a cycloalkoxy group containing from 5 to 8 carbon atoms or an alkylmercapto group containing from 1 to 8 carbon atoms; wherein Alk is a divalent hydrocarbon containing from 1 to 18 carbon atoms; and wherein n is an integer from 2 to 8; said process comprising reacting a compound of the formula Z-Alk-X with the reaction product made by reacting sodium hydroxide with sulfur in a saturated sodium hydroxide solution; wherein X represents a halogen selected from the group consisting of fluorine, chlorine, bromine and iodine; wherein said reaction is carried out in the presence of a phase transfer catalyst; and wherein said reaction is carried out in the presence of a filler.

6. A process for the production of supported organosilicon compounds of the formula

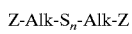

wherein Z is selected from the group consisting of

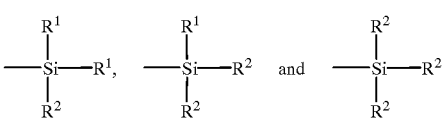

wherein $R^1$ is an alkyl group containing from 1 to 4 carbon atoms, a cyclohexyl group or a phenyl group; wherein $R^2$ is an alkoxy group containing from 1 to 8 carbon atoms, a cycloalkoxy group containing from 5 to 8 carbon atoms or an alkylmercapto group containing from 1 to 8 carbon atoms; wherein Alk represents a divalent hydrocarbon containing from 1 to 18 carbon atoms; wherein X represents a halogen; and wherein n is an integer from 2 to 8; said process comprising the steps of (1) reacting a compound of the formula Z-Alk-X with the reaction product made by reacting sodium hydroxide with sulfur in a saturated sodium hydroxide solution to produce a reaction mixture containing said organosilicon compound; wherein said reaction is carried out in the presence of a phase transfer catalyst; and wherein said process is carried out in the absence of organic solvents; (2) adding a filler to the reaction mixture; and (3) recovering the supported organosilicon compound from the reaction mixture.

7. A process as specified in claim 2 wherein Z is:

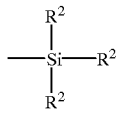

wherein $R^2$ is an alkoxy group containing from 2 to 4 carbon atoms, wherein n is an integer from 2 to 4 and wherein Alk represents a divalent hydrocarbon containing from 2 to 4 carbon atoms.

8. A process as specified in claim 7 wherein X represents chlorine.

9. A process as specified in claim 8 wherein R is an alkoxy group that contains 2 carbon atoms.

10. A process as specified in claim 9 wherein the reaction is carried out at a temperature which is within the range of about 60° C. to about 100° C.

11. A process as specified in claim 2 wherein the phase transfer catalyst is selected from formulae:

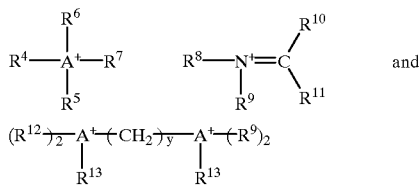

wherein A represents nitrogen, phosphorus or arsenic; $R^4$, $R^5$, $R^6$ and $R^7$, which may be the same or different, are each a linear or branched chain alkyl radical containing from 1 to 16 carbon atoms, optionally substituted with a phenyl, hydroxyl, halo, nitro, alkoxy or alkoxycarbonyl substituent; a linear or branched chain alkenyl radical containing from 2 to 12 carbon atoms; an aryl radical containing from 6 to 10 carbon atoms, optionally substituted by one or more alkyl substituents containing from 1 to 4 carbon atoms or alkoxy, alkoxycarbonyl or halo substituents; and with the proviso that any two of said radicals $R^4$ to $R^7$ may together form a single linear or branched chain alkylene, alkenylene or alkadienylene radical containing from 3 to 6 carbon atoms, $R^8$, $R^9$, $R^{10}$ and $R^{11}$, which also may be the same or different, are each a linear or branched chain alkyl radical containing from 1 to 4 carbon atoms; with the proviso that the $R^{10}$ and $R^{11}$ radicals may together form an alkylene radical containing from 3 to 6 carbon atoms; and with the further proviso that the $R^9$ and $R^{10}$ or $R^9$ and $R^{11}$ radicals may together form an alkylene, alkenylene or alkadienylene radical containing 4 carbon atoms and, together with the nitrogen atom, comprising a 5-membered nitrogen heterocycle; $R^{12}$ is a linear or branched chain alkyl radical containing from 1 to 4 carbon atoms, or a phenyl radical; $R^{13}$ is a linear or branched chain alkyl radical containing from 1 to 4 carbon atoms which may be the same or different from $R^{12}$ or a linear or branched chain alkenyl radical containing from 2 to 12 carbon atoms; and y is an integer from 1 to 10.

12. A process as specified in claim 11 wherein said phase transfer catalyst is selected from the group of cations consisting of tetramethylammonium, triethylmethylammonium, tributylmethylammonium, trimethyl(n-propyl)ammonium, tetraethylammonium, tetrabutylammonium, dodecyltrimethylammonium, methyltrioctylammonium, heptyltributylammonium, tetrapropylammonium, tetrapentylammonium, tetrahexylammonium, tetraheptylammonium, tetraoctylammonium, tetradecylammonium, butyltripropylammonium, methyltributylammonium, pentyltributylammonium, methyldiethylpropylammonium, ethyldimethylpropylammonium, tetradodecylammonium, tetraoctadecylammonium, hexadecyltrimethylammonium, benzyltrimethylammonium, benzyldimethylpropylammonium, benzyldimethyloctylammonium, benzyltributylammonium, benzyltriethylammonium, phenyltrimethylammonium, benzyldimethyltetradecylammonium, benzyldimethylhexadecylammonium, dimethyldiphenylammonium, methyltrialkyl($C_8$-$C_{10}$) ammonium, methyltriphenylammonium, buten-2-yltriethylammonium, N,N-dimethyltetramethyleneammonium, N,N-diethyltetramethyleneammonium, tetramethylphosphonium, tetrabutylphosphonium, ethyltrimethylphosphonium, trimethylpentylphosphonium, trimethylpentylphosphonium, octyltrimethylphosphonium, dodecyltrimethylphosphonium, trimethylphenylphosphonium, diethyldimethylphosphonium, dicyclohexyldimethylphosphonium, dimethyldiphenylphosphonium, cyclohexyltrimethylphosphonium, triethylmethylphosphonium, methyl-tri(isopropyl) phosphonium, methyl-tri(n-propyl)phosphonium, methyl-tri (n-butyl)phosphonium, methyl-tri(2-methylpropyl) phosphonium, methyltricyclohexylphosphonium, methyltriphenylphosphonium, methyltribenzyl phosphonium, methyl-tri(4-methylphenyl)phosphonium, methyltrixylylphosphonium, diethylmethylphenylphosphonium, dibenzylmethylphenylphosphonium, ethyltriphenylphosphonium, tetraethylphosphonium, ethyl-tri(n-propyl)phosphonium, triethylpentylphosphonium, hexadecyltributylphosphonium, ethyltriphenylphosphonium, n-butyl-tri(n-propyl) phosphonium, butyltriphenylphosphonium, benzyltriphenylphosphonium, (β-phenylethyl) dimethylphenylphosphonium, tetraphenylphosphonium, triphenyl(4-methylphenyl)phosphonium, tetrakis (hydroxymethyl)phosphonium, tetrakis(2-hydroxyethyl) phosphonium, tetraphenylarsonium, N-methylpyridinium, N-ethylpyridinium, N-hexadecylpyridinium, N-methylpicolinium, 1,3-bis-2-yldimethylammonium) propane, 1,2-bis(trimethylammonium)ethane, 1,3-bis (trimethylammonium)propane, 1,4-bis (trimethylammonium)butane and 1,3-bis (trimethylammonium)butane and selected from the group of anions consisting of $F^-$, $ClO_4^-$, $PF_6^-$, $BF_4^-$, tetraphenylborate anion, $PO_4^{-3}$, $HPO_4^{-2}$, $H_2PO_4^-$, $CH_3SO_3^-$,

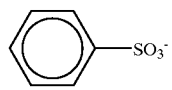

$HSO_4^-$, $NO_3^-$, $SO_4^{-2}$, $Cl^-$ and $Br^-$.

13. A process as specified in claim 2 wherein said phase transfer catalyst is tetrabutyl ammonium bromide.

14. A process as specified in claim 2 wherein said phase transfer catalyst is an onium salt that is present in an amount ranging from 0.1 to 10 mol percent relative to the compound having the formula Z-Alk-X.

15. A process as specified in claim 1 wherein said salt is sodium chloride.

16. A process as specified in claim 15 wherein the sodium chloride salt is present in an amount ranging from 10 weight percent of the aqueous solution to full saturation of the aqueous solution.

17. A technique for reacting a first liquid chemical compound with a second liquid chemical compound which comprises: (1) supporting the first liquid chemical compound on a solid support; (2) subsequently bringing the solid support into contact with the second liquid chemical compound; and (3) allowing the first chemical compound to react with the second chemical compound in the presence of a phase transfer catalyst to produce a reaction product.

18. A technique as specified in claim 17 wherein the reaction product is supported on the solid support.

19. A technique as specified in claim 18 wherein the reaction product which is supported on the solid support is recovered by filtration.

20. A technique as specified in claim 18 wherein said solid support is carbon black.

21. A process as specified in claim 6 wherein the reaction mixture recovered is subsequently dried.

22. A process as specififed in claim 2 wherein the phase transfer catalyst is of the formula:

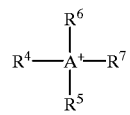

wherein A represents nitrogen, phosphorus or arsenic; wherein $R^4$, $R^5$, $R^6$ and $R^7$ may be the same or different, are each a linear or branched chain alkyl radicals containing from 1 to 16 carbon atoms, optionally substituted with a phenyl, hydroxyl, halo, nitro, alkoxy or alkoxycarbonyl substituent, a linear or branched chain alkenyl radical containing from 2 to 12 carbon atoms, an aryl radical containing from 6 to 10 carbon atoms, optionally substituted by one or more alkyl substituents containing from 1 to 4 carbon atoms or alkoxy, alkoxycarbonyl or halo substituents; and with the proviso that any two of said radicals $R^4$ to $R^7$ may together form a single linear or branched chain alkylene, alkenylene or alkadienylene radical containing from 3 to 6 carbon atoms.

23. A process as specified in claim 2 wherein said phase transfer catalyst is tetrabutyl ammonium bromide.

* * * * *